United States Patent
Koehler

(10) Patent No.: US 12,004,896 B2
(45) Date of Patent: Jun. 11, 2024

(54) SYSTEM AND METHOD FOR X-RAY DARK-FIELD, PHASE CONTRAST AND ATTENUATION IMAGE ACQUISITION

(71) Applicant: KONINKLIJKE PHILIPS N.V., Eindhoven (NL)

(72) Inventor: Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 202 days.

(21) Appl. No.: 17/636,929

(22) PCT Filed: Aug. 21, 2020

(86) PCT No.: PCT/EP2020/073470
§ 371 (c)(1),
(2) Date: Feb. 21, 2022

(87) PCT Pub. No.: WO2021/037706
PCT Pub. Date: Mar. 4, 2021

(65) Prior Publication Data
US 2022/0273257 A1 Sep. 1, 2022

(30) Foreign Application Priority Data
Aug. 23, 2019 (EP) .................... 19193248

(51) Int. Cl.
*A61B 6/58* (2024.01)
*A61B 6/00* (2006.01)
(Continued)

(52) U.S. Cl.
CPC ............ *A61B 6/582* (2013.01); *A61B 6/4035* (2013.01); *A61B 6/4291* (2013.01); *A61B 6/484* (2013.01); *A61B 6/54* (2013.01)

(58) Field of Classification Search
CPC ...... A61B 6/582; A61B 6/4035; A61B 6/4291; A61B 6/484; A61B 6/54
See application file for complete search history.

(56) References Cited

FOREIGN PATENT DOCUMENTS

| JP | H1051813 A | 2/1998 |
|---|---|---|
| JP | 2007143880 A | 6/2007 |

(Continued)

OTHER PUBLICATIONS

PCT International Search Report, International application No. PCT/EP2020/073470, dated Oct. 28, 2020.

(Continued)

*Primary Examiner* — David P Porta
*Assistant Examiner* — Fani Polyzos Boosalis
(74) *Attorney, Agent, or Firm* — Larry Liberchuk

(57) ABSTRACT

The present invention relates to a system (1010) for X-ray dark field, phase contrast and attenuation image acquisition, the system comprising: an X-ray source (1020); an interferometer arrangement (1030); an X-ray detector (1040); a control unit (1050); at least one vibration transducer (1080); a processing unit (1090); and an output unit (1060). An axis is defined extending from a centre of the X-ray source to a centre of the X-ray detector. An examination region is located between the X-ray source and the X-ray detector, wherein the axis extends through the examination region, and wherein the examination region is configured to enable location of an object to be examined. The interferometer arrangement is located between the X-ray source and the X-ray detector, and wherein the interferometer arrangement comprises a first grating (1032) and a second grating (1034). For a first mode of operation: The control unit is configured to control at least one lateral movement transducer (1070) to move the first grating or move the second grating in a lateral (Continued)

position direction perpendicular to the axis. The control unit is configured to control the X-ray detector to acquire image data whilst the first grating and/or second grating is moving. During an exposure time of the X-ray detector the first grating and/or second grating has moved a distance less than a period of the first grating and/or second grating. The control unit is configured to control movement of the first grating and/or second grating such that the image data is acquired whilst the first grating and/or second grating is moving. The output unit is configured to output one or more of: dark field image data, phase contrast image data, and attenuation image data; For a second mode of operation: The control unit is configured to control the X-ray detector to acquire each image data of a plurality of image data whilst the first grating and/or second grating is moving during an exposure time of the X-ray detector. The control unit is configured to control the at least one vibration transducer to vibrate the first grating and/or second grating. An amplitude of vibration is greater than or equal to the period of the first grating and/or second grating. The processing unit is configured to generate attenuation image data and/or calibration data comprising a determination of a temporal low-pass filtered version of at leas some of the plurality of image data. The output unit is configured to output the attenuation image data and/or the calibration data.

9 Claims, 6 Drawing Sheets

(51) Int. Cl.
*A61B 6/40* (2024.01)
*A61B 6/42* (2024.01)

(56) References Cited

FOREIGN PATENT DOCUMENTS

| JP | 2011045655 A | 3/2011 | |
|----|----|----|----|
| JP | JPWO2012057140 A1 | 5/2014 | |
| WO | WO2012147671 A1 | 11/2012 | |
| WO | WO2016177875 A1 | 11/2016 | |
| WO | WO2017013153 A1 | 1/2017 | |
| WO | WO2017013153 A9 | 1/2017 | |
| WO | WO-2017032864 A1 * | 3/2017 | ........... A61B 6/4035 |
| WO | WO-2017191247 A1 * | 11/2017 | ............ A61B 6/463 |
| WO | WO2021037598 A1 | 3/2021 | |

OTHER PUBLICATIONS

Weitkamp T. et al., "X-Ray Phase Imaging with a Grating Interferometer", Optics Express, vol. 13, No. 16, pp. 6296-6304, Aug. 2005.

* cited by examiner

SYSTEM AND METHOD FOR X-RAY DARK-FIELD, PHASE CONTRAST AND ATTENUATION IMAGE ACQUISITION

FIELD OF THE INVENTION

The present invention relates to a system for X-ray dark-field, phase contrast and attenuation image acquisition, to a method for X-ray dark-field, phase contrast and attenuation image acquisition, a system for attenuation image and/or calibration data acquisition, a method for attenuation image and/or calibration data acquisition, as well as to a computer program element and a computer readable medium.

BACKGROUND OF THE INVENTION

Conventional linear attenuation X-ray systems and conventional computed tomography (CT) measure the linear attenuation coefficient of objects. One of the major shortcomings of such conventional techniques is the low contrast between different tissue types, which demands the use of rather high X-ray doses and/or the use of an additional contrast agent.

Grating-based phase-contrast (gbPC) X-ray imaging (both radiography and computed tomography) is a method to provide new X-ray imaging modalities, providing for the simultaneously images of the linear attenuation coefficient, the electron density, and the small angle scattering (i.e., an image obtained from the dark-field signal).

The latter two imaging modalities of X-ray phase-contrast and dark-field imaging are two new imaging modalities that have shown the potential to increase significantly the diagnostic accuracy for soft-tissue imaging. For example, Dark-Field CT (DF-CT) is a new tomographic modality that can visualize anatomical structures below the resolution limit of the detector by quantifying the amount of ultra-small-angle scattering of x-rays by these tiny structures. One of the areas that has been identified to likely benefit most from these two new imaging modalities is chest radiography. It has been shown for example that X-ray dark-field information could significantly help diagnose such pulmonary disorders as chronic obstructive pulmonary disease (COPD) or fibrosis.

For the acquisition of these new imaging modalities a two or three-grating interferometer is introduced into the X-ray beam, normally termed G0, G1 and G2 gratings. The source grating G0, can be used to make radiation from the source more coherent but is not always necessary, and gratings G1 and G2 are normally termed phase and analyzer gratings. Subsequently, one of the two gratings G1 or G2 is moved perpendicular to the grating lamellae relative to the other gratings in a number of steps (so-called stepping), and if the source grating G0 is utilized it can be this grating that is stepped laterally (where laterally means perpendicular to the grating direction). Thereby, for each new grating position an image is recorded. Comparison of the image sequence acquired with and without a sample in the beam, allows to calculate the three imaging signals: transmission or attenuation (conventional X-ray image), phase-contrast image, and dark-field image. At least three images in the sequence (stepping curve) are required in order to calculate the three imaging signals. However, in practice, significantly more images are recorded to allow for a stable signal extraction. These gratings generate a fringe pattern on top of the conventional transmission image, and for example the dark-field signal is calculated as the loss of contrast of this fringe pattern.

Thus, gbPC systems use a stepping acquisition approach. This means that for one multi-modal image several projections are combined. Between each projection one grating is moved to another position to retrieve a stepping curve. These setups concentrate on minimal movement, from for example vibrations, of the gratings during the acquisition to ensure good results. Reproducibility and speed of the repositioning can be a challenge and will always lead to a time gap between two measurements in which the setup is moving and no acquisition is active.

The reason for this is that the fringe-pattern, which is analyzed in gbPC imaging, is a fine structure in the micrometer range. Using an analyzer grating with the same periodicity, a Moiré-pattern can be measured with the detector. Any movement of one or more interferometer components in this length scale changes the phase of the Moiré-pattern. During an exposure a movement leads to blurring and thus degradation of the signal. Here, exposure means the time during which x-rays transmitted through the object are integrated to generate a raw image. This is also called integration period.

State of the art X-ray imaging systems are designed for a structure size several orders of magnitudes larger than this fringe-pattern; hence a standard X-ray system can tolerate much larger vibrations than a gbPC setup. To be able to combine gbPC and conventional CT infrastructure the implementation has to tolerate vibrations. As laboratory gbPC imaging system have been developed in an almost vibration free environment the common acquisition protocol consists of 5 to 30 exposures with exposure times in the magnitude of several seconds. The repositioning-time between exposures is unused, and the system must be stopped and become quiescent before the next image in the stepping curve image set is acquire. Translation of the stepping approach from laboratory to conventional CT struggles with both of these points. On the one hand, the repositioning-time-gap must be shortened to minimize acquisition time. WO 2016/177875 A1 discloses an X-ray imaging system where a faster X-ray acquisition time is possible. On the other hand, the system can no longer be seen as vibration free. This degrades images with long exposure time since the fringe-pattern moves during the measurement.

Another problem arises during calibration protocols like for example detector calibration measurements. For these measurements, it would be best to remove all gratings from the system; however this is not always possible and if done changes the filtration of the X-rays leading to an error in the calibration. In order to acquire and reconstruct quantitatively correct images, accurate calibration data thus needs to be acquired. In conventional CT, highly homogenous elements are placed in the beam, e.g. thin sheets of metal for beam filtration or highly accurately shaped POM to shape the intensity profile of the beam (the so-call wedge filter). The spectral influence of these elements can be calculated analytically thanks to the high precision of these elements. The gratings used for in the new imaging modalities cannot be manufactured with such a high precision. The current state-of-the-art production process is x-ray LIGA, which is a combination of lithography and electroplating. The period of the gratings is manufactured with an extremely high precision—thanks to the high precision that lithographic methods provide. On the other hand, filling grating structures with highly attenuation material like gold or bismuth cannot be done homogeneously enough. Field inhomogeneities during electroplating leads to varying height of the gratings, local defects in the substrate can cause local appearance of additional gold grains on top of the grating. Finally, slight misalignment of a grating in the beam can cause large differences in the spectrum across the beam due to the non-linear partial volume effect. Thus, it is a problem for these new imaging modalities that the spectrum of the x-ray beam cannot be calculated analytically, but it must be measured. However, a measurement of spectral properties is hampered by the fringe pattern generated by the grating arrangement.

There is a need to address these issues.

SUMMARY OF THE INVENTION

It would be advantageous to have improved system for acquiring dark-field, phase contrast, and attenuation X-ray image data, and for determining calibration data of such a system.

The object of the present invention is solved with the subject matter of the independent claims, wherein further embodiments are incorporated in the dependent claims. It should be noted that the following described aspects and examples of the invention apply also to the system for X-ray dark-field, phase contrast and attenuation image acquisition, to the method for X-ray dark-field, phase contrast and attenuation image acquisition, to the system for attenuation image and/or calibration data acquisition, to the method for attenuation image and/or calibration data acquisition as well as for the computer program element and computer readable medium.

In a first aspect, there is provided a system for X-ray dark field, phase contrast and attenuation image acquisition, the system comprising:
an X-ray source;
an interferometer arrangement;
an X-ray detector;
a control unit;
at least one vibration transducer;
a processing unit; and
an output unit.

An axis is defined extending from a centre of the X-ray source to a centre of the X-ray detector. An examination region is located between the X-ray source and the X-ray detector. The axis extending from the centre of the X-ray source to the centre of the X-ray detector also extends through the examination region. The examination region is configured (sized, located and accessible) to enable location of an object to be examined. The interferometer arrangement is located between the X-ray source and the X-ray detector. The interferometer arrangement comprises a first grating and a second grating.

For a first mode of operation:

The control unit is configured to control at least one lateral movement transducer to move the first grating or move the second grating in a lateral position direction perpendicular to the axis. The control unit is configured to control the X-ray detector to acquire image data whilst the first grating and/or second grating is moving. During an exposure time of the X-ray detector the first grating and/or second grating has moved a distance less than a period of the first grating and/or second grating. The control unit is configured to control movement of the first grating and/or second grating such that the image data is acquired whilst the first grating and/or second grating is moving. The output unit is configured to output one or more of: dark field image data, phase contrast image data, and attenuation image data For a second mode of operation:

The control unit is configured to control the X-ray detector to acquire each image data of a plurality of image data whilst the first grating and/or second grating is moving during an exposure time of the X-ray detector. The control unit is configured to control the at least one vibration transducer to vibrate the first grating and/or second grating. An amplitude of vibration is greater than or equal to the period of the first grating and/or second grating. The processing unit is configured to generate attenuation image data and/or calibration data comprising a determination of a temporal low-pass filtered version of at least some of the plurality of image data. The output unit is configured to output the attenuation image data and/or the calibration data.

In other words, an X-ray imaging system is provided with an interferometric arrangement, where a first grating or second grating is moved laterally in order to generate the required stepping curves from which dark field, phase contrast and attenuation image data can be reconstructed, but the one or both of these gratings are intentionally moving during image acquisition, enabled by having an exposure time short enough that the Moiré fringes on the detector are not washed out due to the movement.

In this way, the "stepping" curve image data that can require 5-30 separate images at different lateral positions of the first grating and/or second grating can be acquired more quickly, with reduced X-ray exposure to the patient. This is because the gratings can always be moving, and where for example image data can be acquired as part of the movement to the next position of the 5-30 different positions. Thus, the gratings are not stepped as such, where they are no positioned stationary when image data are acquired but are intentionally moving when image data are acquired, and can indeed be constantly moving.

To put this another way, the system allows for continuous data acquisition in grating-based phase-contrast and dark-field measurements.

In other words, the system in the first mode is operating as a DAX system, where Moiré fringes on the detector are used to generate dark field, phase contrast, and indeed attenuation data, but now in the second mode the fringe pattern, with the gratings still positioned in the beam, is washed out and the system operates in a "normal" attenuation mode, thereby providing for calibration functionality.

In an example, for the first mode of operation, the control unit is configured to control the X-ray detector such that the exposure time is less than a time period of a resonance frequency of vibration of the first grating and/or second grating.

In this manner, in addition to having a short exposure time that enables intentional movement of grating(s) not to wash of the fringe pattern, vibrations of the setup and the repositioning-time-gap are also mitigated due to a decreased acquisition time that is a fraction of the system vibration period. The source of the vibration can be system intrinsic or added via an external device, such as a vibration transducer.

Thus, in the first mode of operation constantly moving grating(s) are utilized with the effect of blurring reduced by reducing exposure times, with the exposure time short enough that the grating movement during one exposure can be effectively neglected. This can be achieved when the exposure times are significantly shorter than the period of the dominant vibration frequency of the gratings. Here constantly moving grating(s) can mean one or more of the gratings moving in a continuous linear movement in one direction and can also mean that one or other or both of the gratings can perform periodic motion.

To put this another way, the system allows for continuous data acquisition in grating-based phase-contrast and dark-field measurements and additionally tolerates external vibrations.

In an example, for the first mode of operation movement of the first grating and/or second grating during the exposure time comprises movement caused by the at least one lateral movement transducer.

Thus, the at least one lateral movement transducer can be continuously moving one or more gratings to the positions for image data collection for dark field and phase contrast image data acquisition. Previously grating movement was required to stop whilst image acquisition occurred, but now image acquisition occurs whilst the gratings are moving between required positions and the overall image acquisition timescale, and patient dosage, is reduced.

In an example, in the second mode of operation application of the low pass filter comprises determination of an average of the at least some of the plurality of image data.

To put this another way, movement of one or both of these gratings by at least this distance and the averaging of acquired data for gratings at different positions in combination with application of a low pass filter leads to the fringes on the detector, that are required for a DAX system, being washed out in the averaged image data. Thus, in one mode of operation the system operates continuously to acquire data in a grating-based phase-contrast and dark-field measurement system with moving grating(s), and in a second mode the system operates as a conventional attenuation image X-ray system that provides for system characterization and calibration without the need to remove the gratings from the beam path.

In an example, the low pass filter comprises a low pass filter kernel having a length greater than the period of vibration of the first grating and/or second grating.

In an example, for the second mode of operation, the control unit is configured to control the X-ray source to periodically move a focal spot on a target to N different target locations, and wherein the control unit is configured to control the X-ray detector to acquire image data separately for each of the N target locations such that the at least some of the plurality of image data relates to one focal spot target location; and wherein the control unit is configured to control the at least one vibration transducer such that a vibration frequency is less that $N/(2T)$, where T is the exposure time of the X-ray detector.

In a second aspect, there is provided a method for X-ray dark field, phase contrast and attenuation image acquisition, the method comprising:
a) orienting an X-ray source relative to an X-ray detector to define an axis extending from a centre of the X-ray source to a centre of the X-ray detector;
b) locating an examination region between the X-ray source and the X-ray detector, wherein the first axis extends through the examination region, and wherein the examination region is configured to enable location of an object to be examined;
c) locating an interferometric arrangement between the X-ray source and the X-ray detector, wherein the interferometer arrangement comprises a first grating and a second grating;
d) in a first mode of operation controlling by a control unit at least one lateral movement transducer to move the first grating or move the second grating in a lateral position direction perpendicular to the axis;
e) in the first mode of operation controlling by the control unit the X-ray detector to acquire image data whilst the first grating and/or second grating is moving, wherein during an exposure time of the X-ray detector the first grating and/or second grating has moved a distance less than a period of the first grating and/or second grating, and wherein the control unit controls movement of the first grating and/or second grating such that the image data is acquired whilst the first grating and/or second grating is moving; and
f) in the first mode of operation outputting by an output unit one or more of: dark field image data, phase contrast image data, and attenuation image data;
g) in a second mode of operation controlling by the control unit the X-ray detector to acquire each image data of a plurality of image data whilst the first grating and/or second grating is moving during an exposure time of the X-ray detector;
h) in the second mode of operation controlling by the control unit at least one vibration transducer to vibrate the first grating and/or second grating, wherein an amplitude of vibration is greater than or equal to the period of the first grating and/or second grating;
i) in the second mode of operation generating by a processing unit attenuation image data and/or calibration data comprising a determination of a temporal low-pass filtered version of at least some of the plurality of image data; and
j) in the second mode of operation outputting by the output unit the attenuation image data and/or the calibration data.

In a third aspect, there is provided a system for attenuation image and/or calibration data acquisition, the system comprising:
an X-ray source;
an interferometer arrangement;
an X-ray detector;
a control unit;
at least one vibration transducer;
a processing unit; and
an output unit.

An axis is defined extending from a centre of the X-ray source to a centre of the X-ray detector. An examination region is located between the X-ray source and the X-ray detector. The axis defined extending from the centre of the X-ray source to the centre of the X-ray detector also extends through the examination region. The examination region is configured (sized, located and accessible) to enable location of an object to be examined. The interferometer arrangement is located between the X-ray source and the X-ray detector. The interferometer arrangement comprises a first grating and a second grating. The control unit is configured to control the X-ray detector to acquire each image data of a plurality of image data whilst the first grating and/or second grating is moving during an exposure time of the X-ray detector. The control unit is configured to control the at least one vibration transducer to vibrate the first grating and/or second grating. An amplitude of vibration is greater than or equal to the period of the first grating and/or second grating. The processing unit is configured to generate attenuation image data and/or calibration data comprising a determination of a temporal low-pass filtered version of at least some of the plurality of image data. The output unit is configured to output the attenuation image data and/or the calibration data.

Thus, during acquisition of a single image data a grating or gratings can move only a small distance due to it being intentionally vibrated, however from one image data to the next the grating or gratings can move further between the images, and using these images together in combination with low pass filtering means that the fringes that would otherwise be present are washed out leaving data that can be utilized for calibration purposes or as an attenuation image in its own right, without having to move the gratings out of the beamline.

In an example, application of the low pass filter comprises determination of an average of the at least some of the plurality of image data.

In an example, the low pass filter comprises a low pass filter kernel having a length greater than the period of vibration of the first grating and/or second grating.

In an example, the control unit is configured to control the X-ray source to periodically move a focal spot on a target to N different target locations. The control unit is configured to control the X-ray detector to acquire image data separately for each of the N target locations. The control unit is configured to control the at least one vibration transducer such that a vibration frequency is less that N/(2T), where T is the exposure time of the X-ray detector In a fourth aspect, there is provided a method for attenuation image and/or calibration data acquisition, the method comprising:
a) locating an X-ray source relative to an X-ray detector to define an axis extending from a centre of the X-ray source to a centre of the X-ray detector, wherein an examination region is located between the X-ray source and the X-ray detector, wherein the first axis extends through the examination region, wherein the examination region enables location of an object to be examined, and wherein an interferometric arrangement is located between the X-ray source and the X-ray detector, wherein the interferometer arrangement comprises a first grating and a second grating;
b) controlling by the control unit the X-ray detector to acquire each image data of a plurality of image data whilst the first grating and/or second grating is moving during an exposure time of the X-ray detector;
c) controlling by the control unit the at least one vibration transducer to vibrate the first grating and/or second grating, wherein an amplitude of vibration is greater than or equal to the period of the first grating and/or second grating;
d) generating by a processing unit attenuation image data and/or calibration data comprising a determination of a temporal low-pass filtered version of at least some of the plurality of image data; and
e) outputting by the output unit the attenuation image data and/or the calibration data In an example, step d) comprises determining an average of the at least some of the plurality of image data.

According to another aspect, there is provided a computer program element controlling a system as previously described which, if the computer program element is executed by a processing unit, is adapted to perform the method steps as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
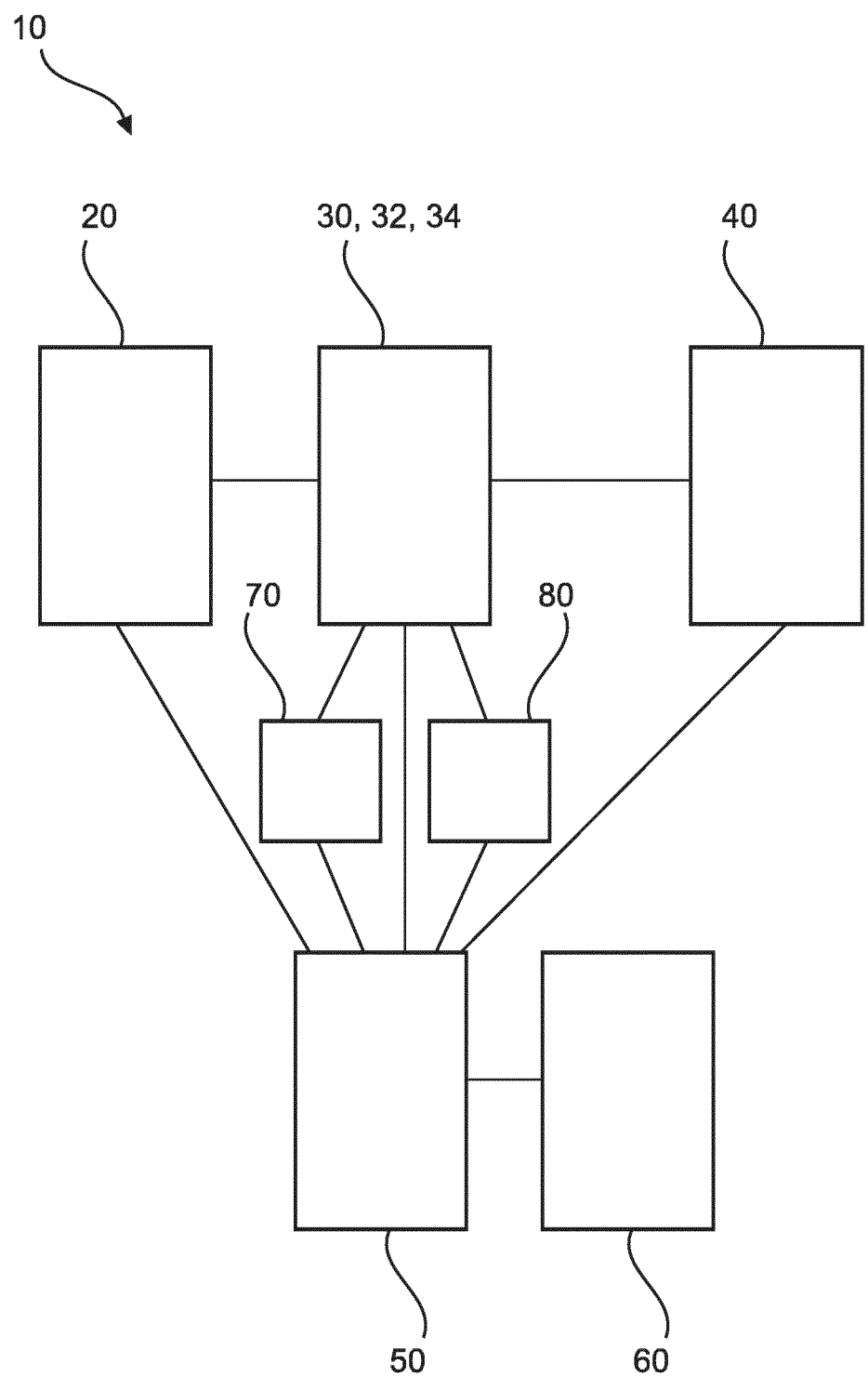
FIG. 1 shows a schematic set up of an example of a system for X-ray dark-field, phase contrast and attenuation image acquisition.

FIG. 1 shows an example of a system 10 for X-ray dark-field, phase contrast and attenuation image acquisition, where not all the features shown are essential as now discussed in more detail. In an example, the system comprises an X-ray source 20, an interferometer arrangement 30, an X-ray detector 40, a control unit 50, and an output unit 60. An axis is defined extending from a centre of the X-ray source to a centre of the X-ray detector. An examination region is located between the X-ray source and the X-ray detector. The axis extends through the examination region, and the examination region is configured to enable location of an object to be examined. The interferometer arrangement is located between the X-ray source and the X-ray detector. The interferometer arrangement comprises a first grating 32 and a second grating 34. For a first mode of operation the control unit is configured to control at least one lateral movement transducer 70 to move the first grating or move the second grating in a lateral position direction perpendicular to the axis. For the first mode of operation the control unit is configured to control the X-ray detector to acquire image data whilst the first grating and/or second grating is moving. For the first mode of operation, during an exposure time of the X-ray detector the control unit is configured to move the first grating and/or second grating a distance less than a period of the first grating and/or second grating. The control unit is configured to control movement of the first grating and/or second grating such that the image data is acquired whilst the first grating and/or second grating is moving. For the first mode of operation the output unit is configured to output one or more of: dark-field image data, phase contrast image data, and attenuation image data.

In other words, an X-ray imaging system is provided with an interferometric arrangement, where a first grating or second grating is moved laterally in order to generate the required stepping curves from which dark-field, phase contrast and attenuation image data can be reconstructed, but the one or both of these gratings are intentionally moving during image acquisition, enabled by having an exposure time short enough that the Moiré fringes on the detector are not washed out due to the movement.

In this way, the "stepping" curve image data that can require 5-30 separate images at different lateral positions of the first grating and/or second grating can be acquired more quickly, with reduced X-ray exposure to the patient. This is because the gratings can always be moving, and where for example image data can be acquired as part of the movement to the next position of the 5-30 different positions. Thus, the gratings are not stepped as such, where they are no positioned stationary when image data are acquired but are intentionally moving when image data are acquired, and can indeed be constantly moving.

To put this another way, the system allows for continuous data acquisition in grating-based phase-contrast and dark-field measurements.

In an example, movement of the first grating or movement of the second grating in a lateral position direction perpendicular to the axis is also perpendicular to grating lines in the grating.

In an example, the first grating is located between the second grating and the X-ray source.

In an example, the examination region is located between the first grating and the X-ray detector.

In an example, the interferometer arrangement comprises three gratings, where a source grating is located to interact with X-rays emitted from the source, and the source grating acts to increase the coherence of the X-ray that propagate through the interferometer arrangement. Thus, without the source grating there can be two gratings, where the first grating is closest to the source and is an absorption grating or a phase grating, and the second grating is closest to the detector and is an absorption grating. However, with three gratings the source grating closest to the source can be the first grating and either of the other two gratings can be the second grating, or the grating above that can be an absorption grating or phase grating can be the first grating etc.

In an example, the first grating is an absorption grating and the second grating is an absorption grating. In an example, the first grating is a phase grating and the second grating is an absorption grating.

According to an example, for the first mode of operation the control unit is configured to control the X-ray detector such that the exposure time is less than a time period of a resonance frequency of vibration of the first grating and/or second grating.

In this manner, in addition to having a short exposure time that enables intentional movement of grating(s) not to wash out the fringe pattern, vibrations of the setup and the repositioning-time-gap are also mitigated due to a decreased acquisition time that is a fraction of the system vibration period. The source of the vibration can be system intrinsic or added via an external device, such as a vibration transducer.

Thus, in the first mode of operation constantly moving grating(s) are utilized with the effect of blurring reduced by reducing exposure times, with the exposure time short enough that the grating movement during one exposure can be effectively neglected. This can be achieved when the exposure times are significantly shorter than the period of the dominant vibration frequency of the gratings. Here constantly moving grating(s) can mean one or more of the gratings moving in a continuous linear movement in one direction and can also mean that one or other or both of the gratings can perform periodic motion.

To put this another way, the system allows for continuous data acquisition in grating-based phase-contrast and dark-field measurements and additionally tolerates external vibrations.

According to an example, for the first mode of operation movement of the first grating and/or second grating during the exposure time comprises movement caused by the at least one lateral movement transducer.

Thus, the at least one lateral movement transducer can be continuously moving one or more gratings to the positions for image data collection for dark-field and phase contrast image data acquisition. Previously grating movement was required to stop whilst image acquisition occurred, but now image acquisition occurs whilst the gratings are moving between required positions and the overall image acquisition timescale, and patient dosage, is reduced.

According to an example, movement of the first grating and/or second grating during the exposure time comprises movement caused by the at least one lateral movement transducer in moving in the lateral position direction as part of an image acquisition protocol.

According to an example, for a second mode of operation the control unit is configured to control the X-ray detector to acquire image data whilst the first grating and/or second grating is moving. For the second mode of operation during an exposure time of the X-ray detector the first grating and/or second grating has moved a distance greater than or equal to the period of the first grating and/or second grating. For the second mode of operation image data is acquired whilst the first grating and/or second grating is moving. For the second mode of operation the output unit is configured to output attenuation image data and/or calibration data.

In other words, the system in the first mode is operating as a DAX system, where Moiré fringes on the detector are used to generate dark-field, phase contrast, and indeed attenuation data, but now in the second mode the fringe pattern, with the gratings still positioned in the beam, is washed out and the system operates in a "normal" attenuation mode, thereby providing for calibration functionality.

To put this another way, movement of one or both of these gratings by at least this distance leads to the fringes on the detector, that are required for a DAX system, being washed out. Thus, in one mode of operation the system operates continuously to acquire data in a grating-based phase-contrast and dark-field measurement system with moving grating(s), and in a second mode the system operates as a conventional attenuation image X-ray system that provides for system characterization and calibration without the need to remove the gratings from the beam path.

The movement of the gratings in the second mode can be intrinsic, such as through dominant or resonance frequency vibrations of the gratings, or intentionally provided via a movement or vibration transducer.

In an example, the vibration transducer can operate all the time, in both the first mode and in the second mode, where the detector exposure time in the first mode is less than the detector exposure time in the second mode.

According to an example, for the second mode of operation the control unit is to control movement of the first grating and/or second grating such that the image data is acquired whilst the first grating and/or second grating is moving.

According to an example, movement of the first grating and/or second grating during the exposure time comprises movement caused by at least one vibration transducer 80 controlled by the control unit. The at least one vibration transducer is configured to vibrate the first grating and/or second grating.

In an example, the at least one vibration transducer is configured to vibrate the first grating and/or second grating with vibrations having an amplitude greater than 10 μm.

Thus, in order to do calibration measurements without a Moiré-pattern but with all gratings in the beam path, a transducer is used to add high frequency and "large" (i.e. several 10 μm) amplitude vibrations to one or more of the gratings. This wipes out all Moiré-fringes from the measurement because even though the exposure time can be very short, with the extra vibration frequency and amplitude the fringe movement leads to extreme blurring of the pattern.

Thus, in the second mode the detector exposure time can be greater than that for the first mode, where in the first mode a movement of the grating(s) at a certain speed that enables Moiré fringes to be detected, now in the second mode with a longer exposure time the fringes are washed out as the grating(s) now move further enabling attenuation data and/or calibration data to be acquired. However, by introducing vibrations to the grating(s) in the second mode the gratings move more in the second mode than in the first mode, and the detector can have the same exposure time in both modes providing for simplified detector electronics and processing. However, in both situations now in the second mode, a fringe pattern that was visible in the first mode is now wiped out, leaving a normal attenuation image that can be used for calibration purposes or provided as a useful attenuation image in its own right.

According to an example, for the second mode of operation movement of the first grating and/or second grating during the exposure time comprises movement caused by the at least one lateral movement transducer.

Thus for example, the lateral movement transducer that operates in the first mode to enable the dark-field and phase contrast data to be acquired can operate in the second mode, where for example a movement at a certain speed in the first mode that is acceptable due to a small exposure time now leads to washing out of the fringes due to a longer exposure time. Or, the transducer can operate in a different manner in the second mode to that in the first, where it imparts faster movements and/or vibration to the gratings in the second mode with respect to the first mode, such that for a constant exposure time between the modes, fringes that are visible in the first mode are washed or wiped out in the second mode.

According to an example, the exposure time for the first mode of operation is equal to the exposure time in the second mode of operation.

According to an example, for the second mode of operation, the control unit is configured to control the X-ray detector such that the exposure time is greater than a time period of a resonance frequency of the first grating and/or second grating.

Referring to the above described system for obtain dark-field, and phase contrast data with associated attenuation data, the system can operate just to acquire attenuation data and/or calibration data by washing out the Moiré fringes. Thus, an example of a system for attenuation image and/or calibration data acquisition comprises an X-ray source 20, an interferometer arrangement 30, an X-ray detector 40, a control unit 50, and an output unit 60. An axis is defined extending from a centre of the X-ray source to a centre of the X-ray detector. An examination region is located between the X-ray source and the X-ray detector. The axis extends through the examination region, and the examination region is configured to enable location of an object to be examined. The interferometer arrangement is located between the X-ray source and the X-ray detector. The interferometer arrangement comprises a first grating 32 and a second grating 34. The control unit is configured to control the X-ray detector to acquire image data whilst the first grating and/or second grating is moving. During an exposure time of the X-ray detector the first grating and/or second grating has moved a distance greater than or equal to a period of the first grating and/or second grating. The output unit is configured to output attenuation image data and/or calibration data.

In an example of the system for attenuation image and/or calibration data acquisition, the control unit is to control movement of the first grating and/or second grating such that the image data is acquired whilst the first grating and/or second grating is moving.

In an example of the system for attenuation image and/or calibration data acquisition, movement of the first grating and/or second grating during the exposure time comprises movement caused by at least one vibration transducer 80 controlled by the control unit, wherein the at least one vibration transducer is configured to vibrate the first grating and/or second grating.

In an example of system for attenuation image and/or calibration data acquisition, the at least one vibration transducer is configured to vibrate the first grating and/or second grating with vibrations having an amplitude greater than 10 μm.

In an example of the system for attenuation image and/or calibration data acquisition, movement of the first grating and/or second grating during the exposure time comprises movement caused by the at least one lateral movement transducer 70. The control unit is configured to control the at least one lateral movement transducer to move the first grating or move the second grating in a lateral position direction perpendicular to the axis.

In an example of the system for attenuation image and/or calibration data acquisition, the control unit is configured to control the X-ray detector such that the exposure time is greater than a time period of a resonance frequency of the first grating and/or second grating.

Figure 2:
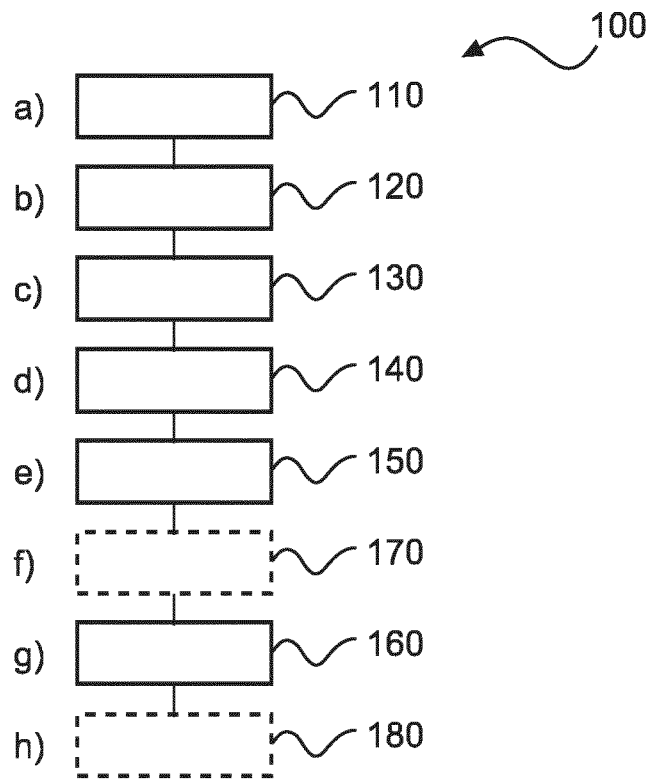
FIG. 2 shows a method for X-ray dark-field, phase contrast and attenuation image acquisition.

FIG. 2 shows an example of a method 100 for X-ray dark-field, phase contrast and attenuation image acquisition in its basic steps. The method 100 comprises: in an orienting step 110, also referred to as step a), orienting an X-ray source 20 relative to an X-ray detector 40 to define an axis extending from a centre of the X-ray source to a centre of the X-ray detector;

in a locating step 120, also referred to as step b), locating an examination region between the X-ray source and the X-ray detector, wherein the first axis extends through the examination region, and wherein the examination region is configured to enable location of an object to be examined;

in a locating step 130, also referred to as step c), locating an interferometric arrangement 30 between the X-ray source and the X-ray detector, wherein the interferometer arrangement comprises a first grating 32 and a second grating 34;

in a first mode of operation:

in a controlling step 140, also referred to as step d), controlling by a control unit 50 at least one lateral movement transducer 70 to move the first grating or move the second grating in a lateral position direction perpendicular to the axis;

in a controlling step 150, also referred to as step e), controlling by the control unit the X-ray detector to acquire image data whilst the first grating and/or second grating is moving, wherein during an exposure time of the X-ray detector the first grating and/or second grating has moved a distance less than a period of the first grating and/or second grating, and wherein the control unit controls movement of the first grating and/or second grating such that the image data is acquired whilst the first grating and/or second grating is moving; and in an outputting step 160, also referred to as step g), outputting by an output unit 60 one or more of: dark-field image data, phase contrast image data, and attenuation image data.

In an example, for the first mode of operation, the method comprises controlling by the control unit the X-ray detector such that the exposure time is less than a time period of a resonance frequency of vibration of the first grating and/or second grating.

In an example, in step e) movement of the first grating and/or second grating during the exposure time comprises movement caused by the at least one lateral movement transducer.

In an example, in step e) movement of the first grating and/or second grating during the exposure time comprises movement caused by the at least one lateral movement transducer in moving in the lateral position direction as part of an image acquisition protocol.

Thus, in an example steps d) and e) can occur at the same time.

According to an example, the method comprises step f) in a second mode of operation: controlling 170 by the control unit the X-ray detector to acquire image data whilst the first grating and/or second grating is moving, wherein during an exposure time of the X-ray detector the first grating and/or second grating has moved a distance greater than or equal to the period of the first grating and/or second grating. The method also comprises step h) in the second mode of operation outputting 180 by the output unit attenuation image data and/or calibration data.

In an example, step f) comprises controlling by the control unit movement of the first grating and/or second grating such that the image data is acquired whilst the first grating and/or second grating is moving.

In an example, in step f) controlling movement of the first grating and/or second grating during the exposure time comprises controlling by the control unit at least one vibration transducer 80 to vibrate the first grating and/or second grating.

In an example, step f) comprises vibrating by the at least one vibration transducer the first grating and/or second grating with vibrations having an amplitude greater than 10 µm.

In an example, step f) comprises moving by the at least one lateral movement transducer the first grating and/or second grating during the exposure time.

In an example, the exposure time in step e) is equal to the exposure time in step f)

In an example, step f) comprises controlling by the control unit the X-ray detector such that the exposure time is greater than a time period of a resonance frequency of the first grating and/or second grating.

Referring to the above described method for obtaining dark-field, and phase contrast data with associated attenuation data, the method can operate just to acquire attenuation data and/or calibration data by washing out the Moiré fringes. Thus, an example of a method for attenuation image and/or calibration data acquisition comprises:

in an orienting step 110, also referred to as step a), orienting an X-ray source 20 relative to an X-ray detector 40 to define an axis extending from a centre of the X-ray source to a centre of the X-ray detector;

in a locating step 120, also referred to as step b), locating an examination region between the X-ray source and the X-ray detector, wherein the first axis extends through the examination region, and wherein the examination region is configured to enable location of an object to be examined;

in a locating step 130, also referred to as step c), locating an interferometric arrangement 30 between the X-ray source and the X-ray detector, wherein the interferometer arrangement comprises a first grating 32 and a second grating 34;

in a controlling step 170, also referred to as step f), controlling by the control unit the X-ray detector to acquire image data whilst the first grating and/or second grating is moving, wherein during an exposure time of the X-ray detector the first grating and/or second grating has moved a distance greater than or equal to a period of the first grating and/or second grating; and in an outputting step 180, also referred to as step h), outputting by the output unit attenuation image data and/or calibration data In an example, step f) comprises controlling by the control unit movement of the first grating and/or second grating such that the image data is acquired whilst the first grating and/or second grating is moving.

In an example, in step f) controlling movement of the first grating and/or second grating during the exposure time comprises controlling by the control unit at least one vibration transducer 80 to vibrate the first grating and/or second grating.

In an example, step f) comprises vibrating by the at least one vibration transducer the first grating and/or second grating with vibrations having an amplitude greater than 10 µm.

In an example, step f) comprises moving by at least one lateral movement transducer the first grating and/or second grating during the exposure time, wherein the control unit is configured to control the at least one lateral movement transducer to move the first grating or move the second grating in a lateral position direction perpendicular to the axis.

In an example, step f) comprises controlling by the control unit the X-ray detector such that the exposure time is greater than a time period of a resonance frequency of the first grating and/or second grating.

As discussed above, with respect to FIGS. 1-2 in a new imaging modality the inter-grating movement required for the stepping curve from which X-ray dark-field and phase-contrast information (along with normal attenuation information) can be determined whilst one or more of the gratings is moving. Thus, stepping curve is referred to here, but the gratings need not be stepped in that they need never be stopped intentionally. This is achieved by moving gratings and reducing the effect of blurring by reduced exposure times. The exposure time has to be short enough that the grating movement during one exposure can be in effect neglected, or at least does not wash out the fringes. This can be guaranteed when the exposure times are significantly shorter than the period of the dominant vibration frequency of the gratings. The vibration of the gratings can be system intrinsic or externally induced e.g. by a vibration transducer. The system can however operate to obtain X-ray attenuation data and/or normal X-ray attenuation data, without having to move the interferometer arrangement out of the beam line. This is done where movement or vibrations of the gratings are large enough to wash out the Moiré fringes. The movement can be that as part of the image acquisition run to acquire data for dark-field, phase contrast and associated attenuation data. And/or the movement can be due to vibrations. The vibration of the gratings can be system intrinsic or externally induced e.g. by a vibration transducer. To be able to do calibration measurements without a Moiré-pattern but with all gratings in the beam path a transducer is used to add high frequency and "large" (i.e. several 10 μm) amplitude vibrations to the gratings. This wipes out all Moiré-fringes from the measurement because even though the exposure time can be very short with the extra vibration frequency and amplitude the fringe movement leads to extreme blurring of the pattern.

However, there is another new manner in which the Moiré fringes can be washed out, as now discussed with respect to FIGS. 3-6.

Figure 3:
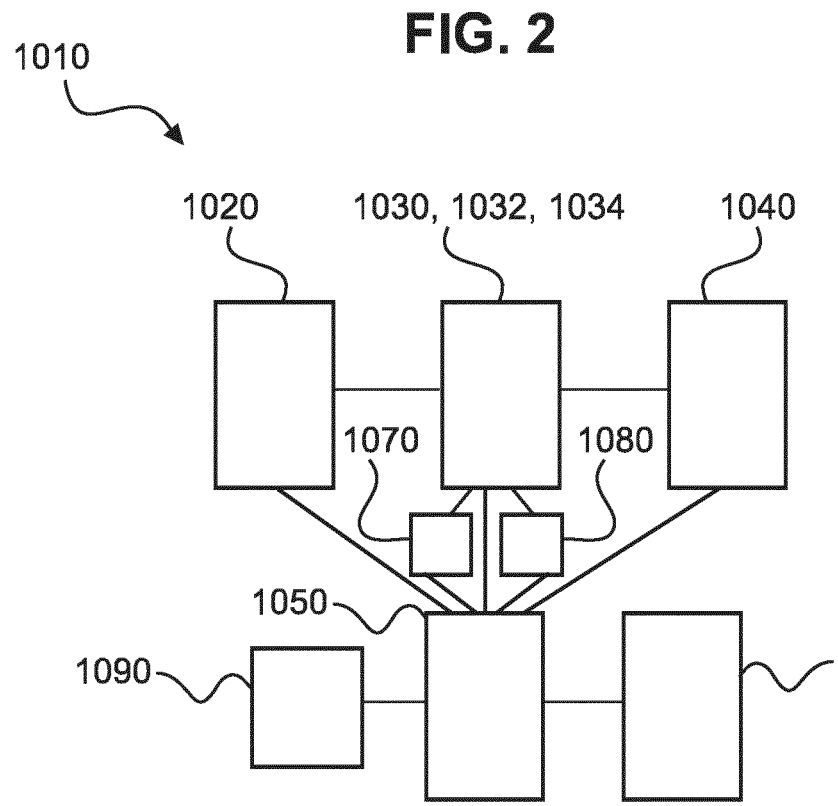
FIG. 3 shows a schematic set up of an example of a system for X-ray dark-field, phase contrast and attenuation image acquisition.

FIG. 3 shows an example of a system 1010 for X-ray dark field, phase contrast and attenuation image acquisition. The system comprises an X-ray source 1020, an interferometer arrangement 1030, an X-ray detector 1040, a control unit 1050, at least one vibration transducer 1080, a processing unit 1090, and an output unit 1060. An axis is defined extending from a centre of the X-ray source to a centre of the X-ray detector. An examination region is located between the X-ray source and the X-ray detector. The axis extending from the centre of the X-ray source to the centre of the X-ray detector also extends through the examination region, and the examination region is configured to enable location of an object to be examined. The interferometer arrangement is located between the X-ray source and the X-ray detector, and the interferometer arrangement comprises a first grating 1032 and a second grating 1034.

For a first mode of operation:

The control unit is configured to control at least one lateral movement transducer 1070 to move the first grating or move the second grating in a lateral position direction perpendicular to the axis. The control unit is configured also to control the X-ray detector to acquire image data whilst the first grating and/or second grating is moving. During an exposure time of the X-ray detector the first grating and/or second grating has moved a distance less than a period of the first grating and/or second grating. The control unit is configured to control movement of the first grating and/or second grating such that the image data is acquired whilst the first grating and/or second grating is moving. The output unit is configured to output one or more of: dark field image data, phase contrast image data, and attenuation image data.

For a second mode of operation:

The control unit is configured to control the X-ray detector to acquire each image data of a plurality of image data whilst the first grating and/or second grating is moving during an exposure time of the X-ray detector. The control unit is configured to control the at least one vibration transducer 1080 to vibrate the first grating and/or second grating. An amplitude of vibration is greater than or equal to the period of the first grating and/or second grating. The processing unit is configured to generate attenuation image data and/or calibration data comprising a determination of a temporal low-pass filtered version of at least some of the plurality of image data. The output unit is configured to output the attenuation image data and/or the calibration data.

In an example, movement of the first grating or movement of the second grating in a lateral position direction perpendicular to the axis is also perpendicular to grating lines in the grating.

In an example, the first grating is located between the second grating and the X-ray source.

In an example, the examination region is located between the first grating and the X-ray detector.

In an example, the interferometer arrangement comprises three gratings, where a source grating is located to interact with X-rays emitted from the source, and the source grating acts to increase the coherence of the X-ray that propagate through the interferometer arrangement. Thus, without the source grating there can be two gratings, where the first grating is closest to the source and is an absorption grating or a phase grating, and the second grating is closest to the detector and is an absorption grating. However, with three gratings the source grating closest to the source can be the first grating and either of the other two gratings can be the second grating, or the grating above that can be an absorption grating or phase grating can be the first grating etc.

In an example, the first grating is an absorption grating and the second grating is an absorption grating. In an example, the first grating is a phase grating and the second grating is an absorption grating.

According to an example, for the first mode of operation, the control unit is configured to control the X-ray detector such that the exposure time is less than a time period of a resonance frequency of vibration of the first grating and/or second grating.

According to an example, for the first mode of operation movement of the first grating and/or second grating during the exposure time comprises movement caused by the at least one lateral movement transducer.

In an example, movement of the first grating and/or second grating during the exposure time comprises movement caused by the at least one lateral movement transducer in moving in the lateral position direction as part of an image acquisition protocol.

According to an example, in the second mode of operation application of the low pass filter comprises determination of an average of the at least some of the plurality of image data.

In an example, the at least one vibration transducer is configured to vibrate the first grating and/or second grating with vibrations having an amplitude greater than 10 μm.

Thus, in order to do calibration measurements without a Moiré-pattern but with all gratings in the beam path a transducer is used to add high frequency and "large" (i.e. several 10 μm) amplitude vibrations to one or more of the gratings. Averaging of acquired data for each focal spot position leads to wiping out all Moiré-fringes from the measurement because even though the exposure time can be very short, with the extra vibration frequency and amplitude the fringe movement between images leads to extreme blurring of the pattern. Such blurring is further increased through low pass filtering of the image data.

In an example, the exposure time for the first mode of operation is equal to the exposure time in the second mode of operation.

According to an example, the low pass filter comprises a low pass filter kernel having a length greater than the period of vibration of the first grating and/or second grating.

According to an example, for the second mode of operation, the control unit is configured to control the X-ray source to periodically move a focal spot on a target to N different target locations, and wherein the control unit is configured to control the X-ray detector to acquire image data separately for each of the N target locations such that the at least some of the plurality of image data relates to one focal spot target location; and wherein the control unit is configured to control the at least one vibration transducer such that a vibration frequency is less that N/(2T), where T is the exposure time of the X-ray detector.

Figure 4:
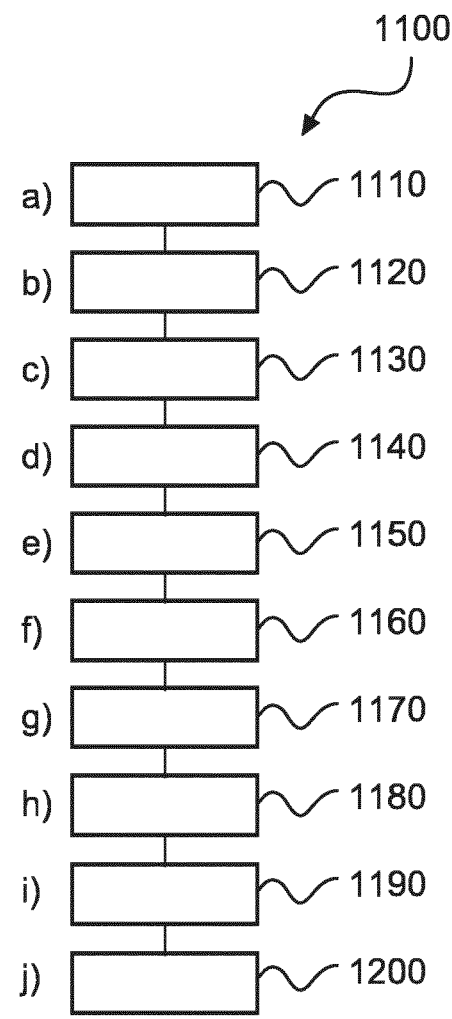
FIG. 4 shows a method for X-ray dark-field, phase contrast and attenuation image acquisition.

FIG. 4 shows a method 1100 for X-ray dark field, phase contrast and attenuation image acquisition in its basic steps. The method comprises:

in an orienting step 1110, also referred to as step a), orienting an X-ray source 1020 relative to an X-ray detector 1040 to define an axis extending from a centre of the X-ray source to a centre of the X-ray detector;

in a locating step 1120, also referred to as step b), locating an examination region between the X-ray source and the X-ray detector, wherein the first axis extends through the examination region, and wherein the examination region is configured to enable location of an object to be examined;

in a locating step 1130, also referred to as step c), locating an interferometric arrangement 1030 between the X-ray source and the X-ray detector, wherein the interferometer arrangement comprises a first grating 1032 and a second grating 1034;

in a first mode of operation:

in a controlling step 1140, also referred to as step d), controlling by a control unit 1050 at least one lateral movement transducer 1070 to move the first grating or move the second grating in a lateral position direction perpendicular to the axis;

in a controlling step 1150, also referred to as step e), controlling 1150 by the control unit the X-ray detector to acquire image data whilst the first grating and/or second grating is moving, wherein during an exposure time of the X-ray detector the first grating and/or second grating has moved a distance less than a period of the first grating and/or second grating, and wherein the control unit controls movement of the first grating and/or second grating such that the image data is acquired whilst the first grating and/or second grating is moving; and in an outputting step 1160, also referred to as step f), outputting by an output unit (1060) one or more of: dark field image data, phase contrast image data, and attenuation image data;

in a second mode of operation:

in a controlling step 1170, also referred to as step g), controlling by the control unit the X-ray detector to acquire each image data of a plurality of image data whilst the first grating and/or second grating is moving during an exposure time of the X-ray detector;

in a controlling step 1180, also referred to as step h), controlling by the control unit at least one vibration transducer 1080 to vibrate the first grating and/or second grating, wherein an amplitude of vibration is greater than or equal to the period of the first grating and/or second grating;

in a generating step 1190, also referred to as step i), generating by a processing unit attenuation image data and/or calibration data comprising a determination of a temporal low-pass filtered version of at least some of the plurality of image data; and in a outputting step 1200, also referred to as step j), outputting by the output unit the attenuation image data and/or the calibration data.

In an example, for the first mode of operation, the method comprises controlling by the control unit the X-ray detector such that the exposure time is less than a time period of a resonance frequency of vibration of the first grating and/or second grating.

In an example, in step e) movement of the first grating and/or second grating during the exposure time comprises movement caused by the at least one lateral movement transducer.

In an example, in step e) movement of the first grating and/or second grating during the exposure time comprises movement caused by the at least one lateral movement transducer in moving in the lateral position direction as part of an image acquisition protocol.

Thus, in an example steps d) and e) can occur at the same time.

In an example, step h) comprises vibrating by the at least one vibration transducer the first grating and/or second grating with vibrations having an amplitude greater than 10 µm.

In an example, the exposure time in step e) is equal to the exposure time in step h)

In an example, step i) comprises determining an average of the at least some of the plurality of image data.

In an example, the low pass filter comprises a low pass filter kernel having a length greater than the period of vibration of the first grating and/or second grating.

In an example, step g) comprises controlling by the control unit the X-ray source to periodically move a focal spot on a target to N different target locations, and wherein the control unit is configured to control the X-ray detector to acquire image data separately for each of the N target locations such that the at least some of the plurality of image data relates to one focal spot target location; and wherein step h) controlling the at least one vibration transducer such that a vibration frequency is less that N/(2T), where T is the exposure time of the X-ray detector such that the exposure time is greater than a time period of a resonance frequency of the first grating and/or second grating.

Figure 5:
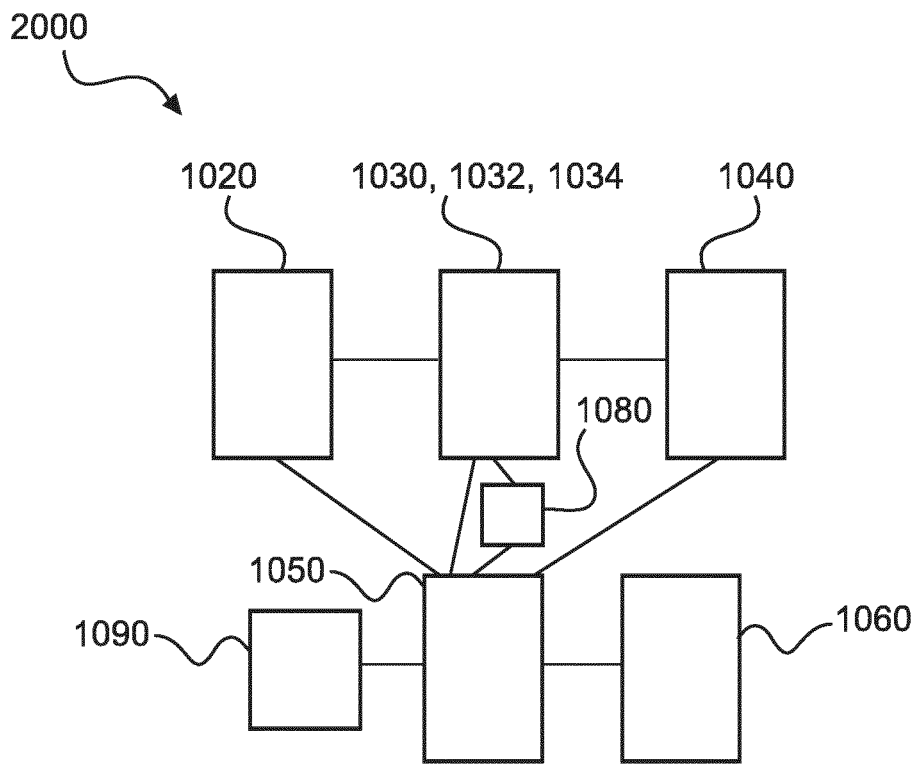
FIG. 5 shows a schematic set up of an example of a system for attenuation image and/or calibration data acquisition.

FIG. 5 shows an example of a system 2000 for attenuation image and/or calibration data acquisition. The system comprises an X-ray source 1020, an interferometer arrangement 1030, an X-ray detector 1040, a control unit 1050, at least one vibration transducer 1080, a processing unit 1090, and an output unit 1060. An axis is defined extending from a centre of the X-ray source to a centre of the X-ray detector. An examination region is located between the X-ray source and the X-ray detector. The axis extending from the centre of the X-ray source to the centre of the X-ray detector also extends through the examination region, and the examination region is configured to enable location of an object to be examined. Thus, the examination region is located such that an object can be positioned there for examination. The interferometer arrangement is located between the X-ray source and the X-ray detector, and the interferometer arrangement comprises a first grating 1032 and a second grating 1034. The control unit is configured to control the X-ray detector to acquire each image data of a plurality of image data whilst the first grating and/or second grating is moving during an exposure time of the X-ray detector. The control unit is configured also to control the at least one vibration transducer 1080 to vibrate the first grating and/or second grating. An amplitude of vibration is greater than or equal to the period of the first grating and/or second grating. The processing unit is configured to generate attenuation image data and/or calibration data comprising a determination of a temporal low-pass filtered version of at least some of the plurality of image data. The output unit is configured to output the attenuation image data and/or the calibration data.

In an example, the at least one vibration transducer is configured to vibrate the first grating and/or second grating with vibrations having an amplitude greater than 10 µm.

According to an example, application of the low pass filter comprises determination of an average of the at least some of the plurality of image data.

According to an example, the low pass filter comprises a low pass filter kernel having a length greater than the period of vibration of the first grating and/or second grating.

Figure 6:
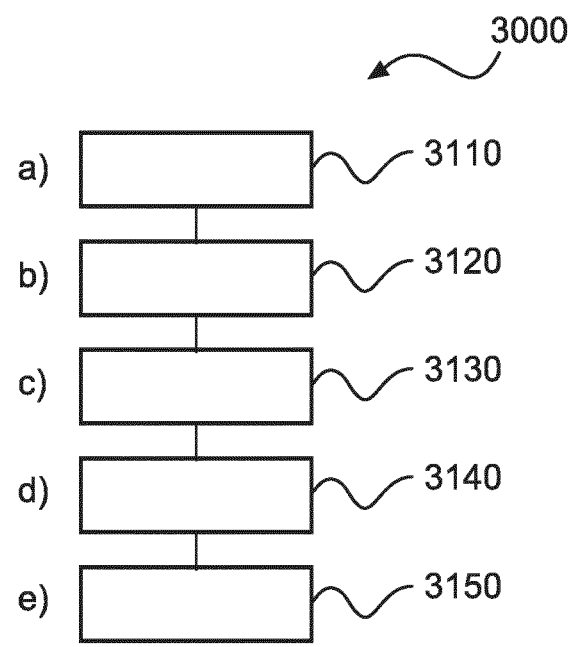
FIG. 6 shows a method for attenuation image and/or calibration data acquisition.

According to an example, the control unit is configured to control the X-ray source to periodically move a focal spot on a target to N different target locations, and wherein the control unit is configured to control the X-ray detector to acquire image data separately for each of the N target locations; and wherein the control unit is configured to control the at least one vibration transducer such that a vibration frequency is less that N/(2T), where T is the exposure time of the X-ray detector FIG. 6 shows a method 3000 for attenuation image and/or calibration data acquisition in its basic steps. The method comprises:

in a locating step 3110, also referred to as step a), locating an X-ray source 1020 relative to an X-ray detector 1040 to define an axis extending from a centre of the X-ray source to a centre of the X-ray detector, wherein an examination region is located between the X-ray source and the X-ray detector, wherein the first axis extends through the examination region, wherein the examination region enables location of an object to be examined, and wherein an interferometric arrangement 1030 is located between the X-ray source and the X-ray detector, wherein the interferometer arrangement comprises a first grating 1032 and a second grating 1034;

in a controlling step 3120, also referred to as step b), controlling by the control unit the X-ray detector to acquire each image data of a plurality of image data whilst the first grating and/or second grating is moving during an exposure time of the X-ray detector;

in a controlling step 3130, also referred to as step c), controlling by the control unit the at least one vibration transducer 1080 to vibrate the first grating and/or second grating, wherein an amplitude of vibration is greater than or equal to the period of the first grating and/or second grating;

in a generating step 3140, also referred to as step d), generating by a processing unit 1090 attenuation image data and/or calibration data comprising a determination of a temporal low-pass filtered version of at least some of the plurality of image data; and in an outputting step 3150, also referred to as step e), outputting by the output unit the attenuation image data and/or the calibration data In an example, step b) comprises vibrating by the at least one vibration transducer the first grating and/or second grating with vibrations having an amplitude greater than 10 μm.

According to an example, step d) comprises determining an average of the at least some of the plurality of image data.

In an example, the low pass filter comprises a low pass filter kernel having a length greater than the period of vibration of the first grating and/or second grating.

In an example, step b) comprises controlling by the control unit the X-ray source to periodically move a focal spot on a target to N different target locations, and wherein the control unit controls the X-ray detector to acquire image data separately for each of the N target locations; and wherein step c) comprises controlling the control unit control the at least one vibration transducer such that a vibration frequency is less that N/(2T), where T is the exposure time of the X-ray detector Thus, with reference to FIGS. 3-6 for the acquisition of calibration data and/or an attenuation image itself, the fringe pattern is eliminated through a combination of in effect two techniques. The first is still a vibration imposed onto at least one of the gratings, where the amplitude is at least equal to the grating period. This ensures that the fringe pattern oscillates at least by 360°. The second element is to average detector readings for each focal spot position. Specifically, for a quad-focal spot acquisition, where the focal spot of the x-ray tube moves periodically between four different locations on the anode, the signal for each focal spot position is low-pass filtered in time. Some specific further details are:

the size of the low-pass kernel should be large enough to capture at least one period of the dominant vibration frequency.

If the integration period of the detector is T, the Nyquist frequency of the detector is 1/2T. However, for a quad-focus acquisition, only every fourth readout is used in the averaging. Thus, the vibration frequency should be well below 2/T in order to avoid aliasing problems.

Calibration information can be obtained for instance by placing different homogenous material into the beam during the calibration measurement.

Aspects of the new imaging modality is further explained with reference to FIGS. 7-8.

Figure 7:
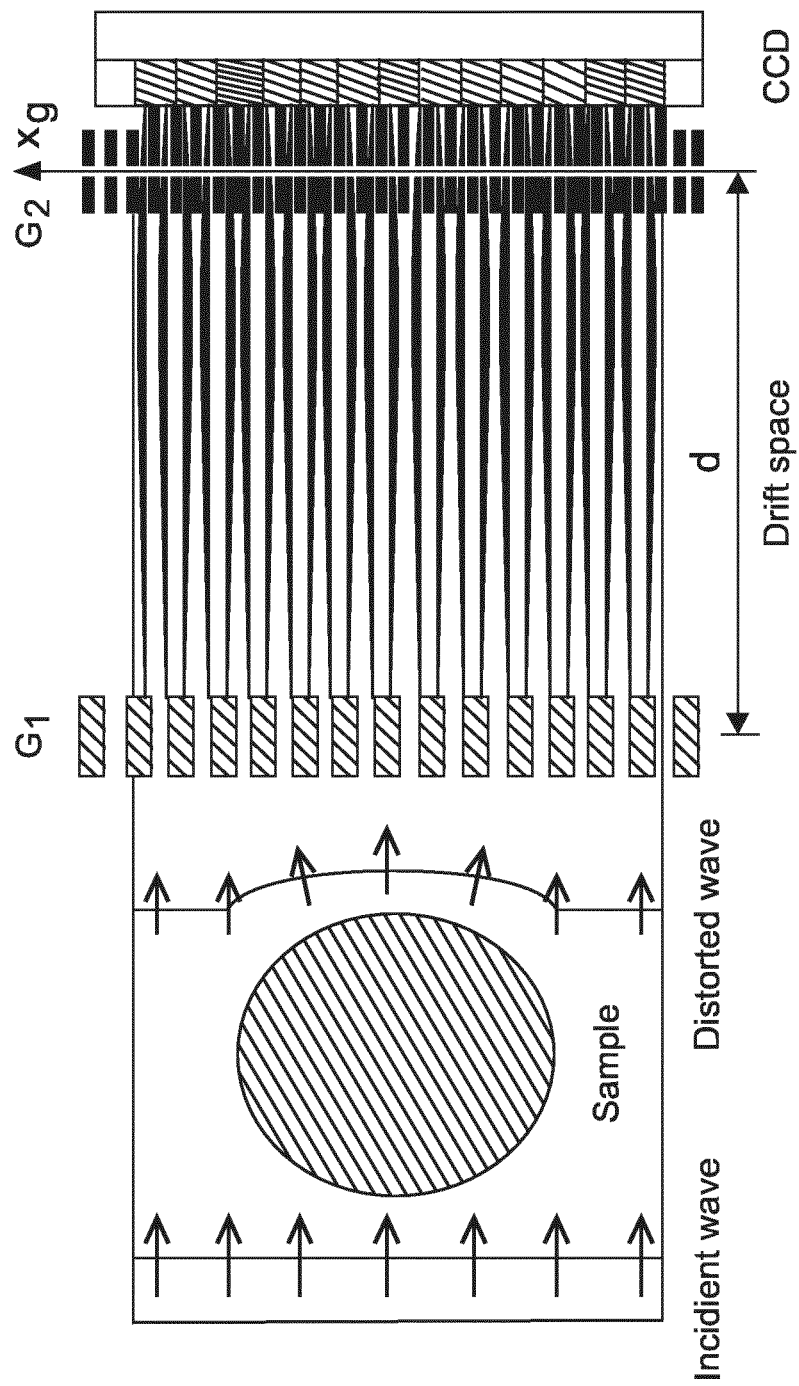
FIG. 7 shows a schematic set up of an example of a phase-contrast, dark-field and attenuation imaging system.
Figure 8:
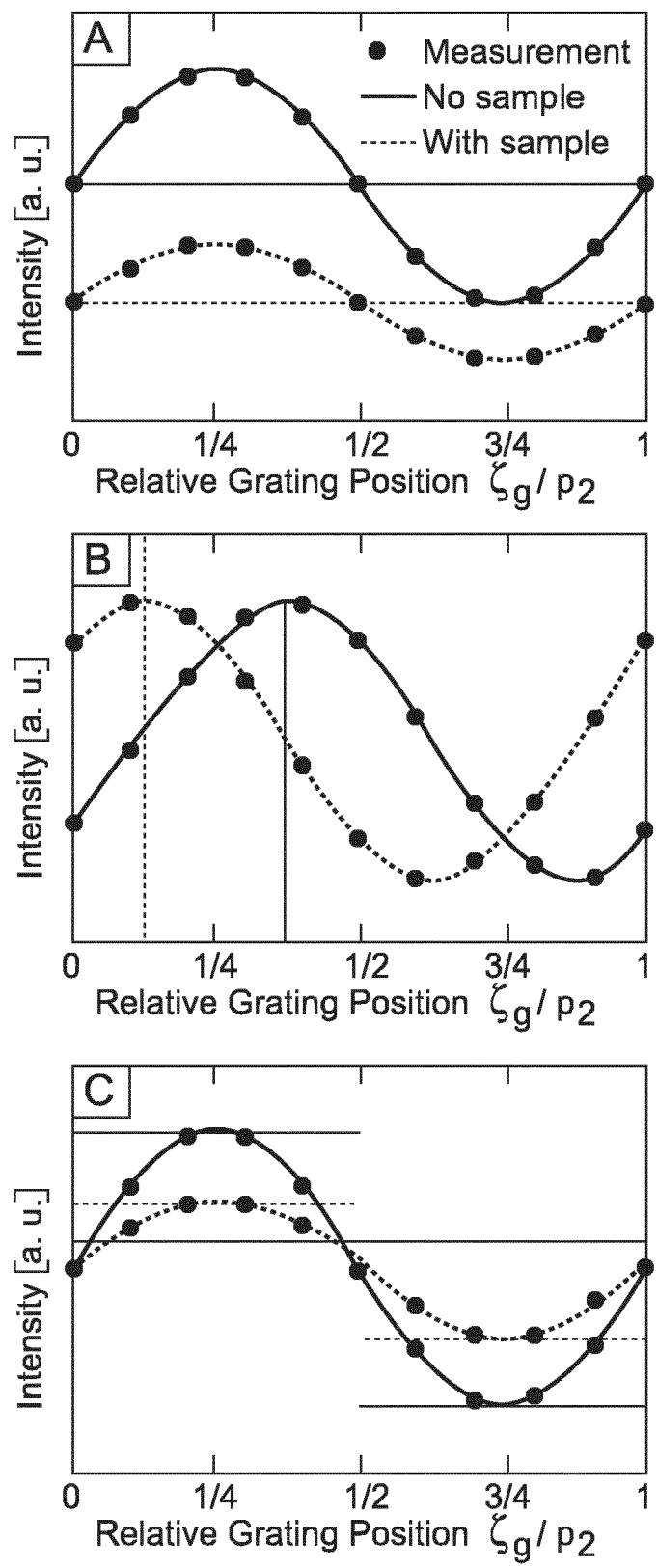
FIG. 8 shows stepping curve data obtained by the imaging system of FIG. 7.

FIG. 7 shows an example of the interferometer part of the system that can acquire X-ray phase contrast, dark-field and attenuation image data. Reference to interferometer arrangement above, refers only to the gratings of the interferometer part of the system. The system is capable of imaging for the spatial distribution of attenuation of, or in, the sample and also at the same time capable of imaging for the spatial distribution of refraction (phase-contrast imaging) and also capable of imaging for the spatial distribution of small angle scattering (dark-field imaging). The system has a grating based interferometer. In this example, the interferometer comprises two grating structures G1 and G2, although in other examples a three grating interferometer (having gratings G0, G1 and G2) is used, where the source grating G0 near to the source is used to increase the coherence of radiation propagating through the sample and G1 and G2 gratings.

In FIG. 7, the source grating G0 is not shown and the discussion that follows considers a two grating structure G1 and G2, although all three of G0, G1 and G2 can be present, and where G0 can be the grating that is moved laterally. In FIG. 7 the grating G1 is a phase grating (but also can be an absorption grating) whereas G2 is an absorption gating. The system further comprises an X-ray source and the X-ray detector. The X-ray detector, here shown as a CCD detector, can be a 2D full view X-ray detector, which is either planar or curved. A plurality of detector pixels are arranged in rows and columns as an array to form a 2D X-ray radiation sensitive surface capable of registering X-ray radiation emitted by the X-ray source. The X-ray detector and the X-ray source are spaced apart to form an examination region. The examination region is suitably spaced to receive the sample to be imaged. The sample can be for example a patient's breast, or a patient's chest in order to examine the lung. Either of G1 or G2 can be curved or flat, but even if curved a plane can be defined that is parallel to the centre of the grating. The system has a transducer to move a grating laterally, and can also have a vibration transducer to vibrate one of the gratings.

The sample then modulates attenuation, refraction, and small angle scattering information onto the radiation, which can then be extracted by operation of the grating tandem G1 and G2. The gratings G1, G2 induce an interference pattern, which can be detected at the X-ray detector as fringes of a Moiré pattern. If there were no object in the examination region, there would still be an interference patter observable at the X-ray detector, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the sample is positioned in the examination region and interacts with the radiation as mentioned, the Moiré pattern, which is now more appropriately called the sample pattern, can be understood as a disturbed version of the reference pattern.

To separate this phase information from other contributions to the signal, such as attenuation by the sample, inhomogeneous illumination or imperfections of the gratings, a modified phase—"stepping" approach is utilized. One of the gratings (either G1 or G2—or G0 if present) is scanned along the transverse direction $x_g$ (as shown in FIG. 3) over at least one period of the grating, and for every point of the scan an image is taken and this image data is acquired whilst the grating is moving, with a detector exposure time such that the Moiré fringes are not washed out. If the source grating G0 is present, it can be this grating that is scanned along the transverse direction. The resultant phase contrast, dark-field, and attenuation data then oscillates sinusoidal, with and without the sample, as shown in FIG. 8 for phase-contrast (A), dark-field (B), and attenuation (C). Further detail on the standard phase stepping approach can be found in the paper by Weitkamp et al, Optics Express, Vol. 13, No. 16, (2005) 6296-6304.

However, for the currently described system another mode of operation is utilized to obtain X-ray calibration data, or normal attenuation data. The grating that is being moved as described above can be moved in the same way by the lateral movement transducer, but the detector exposure time can be increased to wash out the fringes. Also, the movement speed could be increased for a constant detector exposure time. There are a combination of movement speeds and exposure times that lead to washing out of the fringes, as would be readily appreciated. However, another way of washing out the fringes is just to increase the exposure time to a duration at which the fringes was out, as a result of intrinsic vibrations of the system. These vibrations can be augmented through utilization of a vibration transducer to vibrate laterally a grating, such that for the detector exposure time being used the Moiré fringes are washed out.

Furthermore, in a different technique a system can be used to obtain X-ray calibration data, or normal attenuation data whilst the gratings remain in position. This technique vibrates the gratings, which do not need to move much or at all during image acquisition. However, the amplitude of vibration is sufficient such that in combination with low pass filtering, a number of images can be combined. However, now at least one grating has moved from at least one previous image acquisition position, and this enables the fringes that would otherwise be present to be washed out or removed. This then results in data that can be used for calibration purposes or just as a normal attenuation image.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:
1. A system for X-ray dark field, phase contrast and attenuation image acquisition, the system comprising:
- an X-ray source;
- an interferometer;
- an X-ray detector;
- a controller;
- at least one vibration transducer;
- a processor; and
- an output;
- wherein an axis is defined extending from a center of the X-ray source to a center of the X-ray detector;
- wherein an examination region is located between the X-ray source and the X-ray detector, wherein the axis extends through the examination region, and wherein the examination region is configured to enable location of an object to be examined;
- wherein the interferometer is located between the X-ray source and the X-ray detector, and wherein the interferometer comprises a first grating and a second grating;
- wherein for a first mode of operation:
  - the controller is configured to control at least one lateral movement transducer to move the first grating or move the second grating in a lateral position direction perpendicular to the axis; and
  - wherein the controller is configured to control the X-ray detector to acquire image data whilst the first grating and/or second grating is moving, wherein during an exposure time of the X-ray detector the first grating and/or second grating has moved a distance less than a period of the first grating and/or second grating, and wherein the controller is configured to control movement of the first grating and/or second grating such that the image data is acquired whilst the first grating and/or second grating is moving; and
  - wherein for the first mode of operation the output is configured to output one or more of: dark field image data, phase contrast image data, and attenuation image data;
- wherein for a second mode of operation:
  - the controller is configured to control the X-ray detector to acquire each image data of a plurality of image data whilst the first grating and/or second grating is moving during an exposure time of the X-ray detector;
  - the controller is configured to control the at least one vibration transducer to vibrate the first grating and/or second grating, wherein an amplitude of vibration is greater than or equal to the period of the first grating and/or second grating;
  - the processor is configured to generate attenuation image data and/or calibration data comprising a determination of a temporal low-pass filtered version of at least some of the plurality of image data; and
  - wherein for the second mode of operation the output is configured to output the attenuation image data and/or the calibration data.

2. The system according to claim 1, wherein for the first mode of operation, the controller is configured to control the X-ray detector such that the exposure time is less than a time period of a resonance frequency of vibration of the first grating and/or second grating.

3. The system according to claim 1, wherein for the first mode of operation movement of the first grating and/or second grating during the exposure time comprises movement caused by the at least one lateral movement transducer.

4. The system according to claim 1, wherein in the second mode of operation application of the low pass filter comprises determination of an average of the at least some of the plurality of image data.

5. The system according to claim 4, wherein the low pass filter comprises a low pass filter kernel having a length greater than the period of vibration of the first grating and/or second grating.

6. The system according to claim 4, wherein for the second mode of operation, the controller is configured to control the X-ray source to periodically move a focal spot on a target to N different target locations, and wherein the controller is configured to control the X-ray detector to acquire image data separately for each of the N target locations such that the at least some of the plurality of image data relates to one focal spot target location; and wherein the controller is configured to control the at least one vibration transducer such that a vibration frequency is less that N/(2T), where T is the exposure time of the X-ray detector.

7. A method for X-ray dark field, phase contrast and attenuation image acquisition, the method comprising:
- orienting an X-ray source relative to an X-ray detector to define an axis extending from a center of the X-ray source to a center of the X-ray detector;
- locating an examination region between the X-ray source and the X-ray detector, wherein the first axis extends through the examination region, and wherein the examination region is configured to enable location of an object to be examined;
- locating an interferometer between the X-ray source and the X-ray detector, wherein the interferometer comprises a first grating and a second grating;
- in a first mode of operation controlling at least one lateral movement transducer to move the first grating or move the second grating in a lateral position direction perpendicular to the axis;
- in the first mode of operation controlling the X-ray detector to acquire image data whilst the first grating and/or second grating is moving, wherein during an exposure time of the X-ray detector the first grating and/or second grating has moved a distance less than a period of the first grating and/or second grating, and wherein movement of the first grating and/or second grating is controlled such that the image data is acquired whilst the first grating and/or second grating is moving; and
- outputting one or more of: dark field image data, phase contrast image data, and attenuation image data;
- in a second mode of operation controlling the X-ray detector to acquire each image data of a plurality of image data whilst the first grating and/or second grating is moving during an exposure time of the X-ray detector;
- in the second mode of operation controlling at least one vibration transducer to vibrate the first grating and/or second grating, wherein an amplitude of vibration is greater than or equal to the period of the first grating and/or second grating;
- in the second mode of operation generating attenuation image data and/or calibration data comprising a determination of a temporal low-pass filtered version of at least some of the plurality of image data; and
- outputting the attenuation image data and/or the calibration data.

8. A method for attenuating image and/or calibration data, the method comprising:
- locating an X-ray source relative to an X-ray detector to define an axis extending from a center of the X-ray source to a center of the X-ray detector, wherein an examination region is located between the X-ray source and the X-ray detector, wherein the first axis extends through the examination region, wherein the examination region enables location of an object to be examined, and wherein an interferometer is located between the X-ray source and the X-ray detector, wherein the interferometer comprises a first grating and a second grating;
- controlling the X-ray detector to acquire each image data of a plurality of image data whilst the first grating and/or second grating is moving during an exposure time of the X-ray detector;
- controlling the at least one vibration transducer to vibrate the first grating and/or second grating, wherein an amplitude of vibration is greater than or equal to the period of the first grating and/or second grating;
- generating the attenuation image data and/or calibration data comprising a determination of a temporal low-pass filtered version of at least some of the plurality of image data; and
- outputting the attenuation image data and/or the calibration data.

9. The method according to claim 8, further comprising determining an average of the at least some of the plurality of image data.

* * * * *